(12) United States Patent
Trivedi et al.

(10) Patent No.: US 8,900,644 B2
(45) Date of Patent: Dec. 2, 2014

(54) ORAL CARE COMPOSITIONS CONTAINING COMPOUNDS FROM MAGNOLIA AND HOPS EXTRACTS

(75) Inventors: Harsh M. Trivedi, Somerset, NJ (US);
Tao Xu, East Brunswick, NJ (US);
Susan Herles, Flemington, NJ (US)

(73) Assignee: Colgate-Palmolive Company, New York, NY (US)

( * ) Notice: Subject to any disclaimer, the term of this patent is extended or adjusted under 35 U.S.C. 154(b) by 697 days.

(21) Appl. No.: 11/244,693

(22) Filed: Oct. 6, 2005

(65) Prior Publication Data
US 2006/0134024 A1 Jun. 22, 2006

Related U.S. Application Data

(60) Provisional application No. 60/639,330, filed on Dec. 22, 2004.

(51) Int. Cl.
| | | |
|---|---|---|
| *A61K 36/899* | (2006.01) | |
| *A61Q 11/00* | (2006.01) | |
| *A61K 8/34* | (2006.01) | |
| *A61K 8/35* | (2006.01) | |
| *A61K 8/97* | (2006.01) | |

(52) U.S. Cl.
CPC ............. *A61Q 11/00* (2013.01); *A61K 8/347* (2013.01); *A61K 8/35* (2013.01); *A61K 8/97* (2013.01)
USPC ....................................................... 424/750

(58) Field of Classification Search
None
See application file for complete search history.

(56) References Cited

U.S. PATENT DOCUMENTS

| | | | |
|---|---|---|---|
| 3,932,603 A | | 1/1976 | Haas |
| 4,454,163 A | | 6/1984 | Gellman et al. |
| 4,454,164 A | | 6/1984 | Gellman et al. |
| 5,000,943 A | | 3/1991 | Scaglione et al. |
| 5,082,975 A | | 1/1992 | Todd, Jr. et al. |
| 5,165,447 A | | 11/1992 | Arbjerg et al. |
| 5,180,577 A | | 1/1993 | Polefka et al. |
| 5,370,863 A | * | 12/1994 | Barney et al. ............. 424/49 |
| 5,405,836 A | | 4/1995 | Richar et al. |
| 5,980,869 A | | 11/1999 | Sanker et al. |
| 6,005,409 A | | 12/1999 | Bui et al. |
| 6,129,907 A | | 10/2000 | Sreenivasan et al. |
| 6,165,447 A | * | 12/2000 | Trivedi et al. ............. 424/49 |
| 6,165,477 A | * | 12/2000 | Ivy et al. ............... 424/218.1 |
| 6,290,933 B1 | | 9/2001 | Durga et al. |
| 6,500,409 B1 | * | 12/2002 | Scherl et al. ................ 424/58 |
| 6,685,921 B2 | | 2/2004 | Lawlor |
| 2003/0206874 A1 | | 11/2003 | Doyle et al. |

FOREIGN PATENT DOCUMENTS

| | | | |
|---|---|---|---|
| CN | 1318362 A | * | 10/2001 |
| CN | 1331968 A | * | 1/2002 |
| JP | 01151512 A | * | 6/1989 |
| JP | 04091029 A | * | 3/1992 |
| JP | 03-121036 | | 12/2000 |
| JP | 2003113013 A | * | 4/2003 |
| JP | 2003231647 A | * | 8/2003 |
| WO | WO 97/35599 | | 10/1997 |
| WO | WO 0182922 A1 | * | 11/2001 |
| WO | WO 02/091848 | | 11/2002 |

OTHER PUBLICATIONS

Marsh, P.D. Microbiologic aspects of dental plaque and dental caries. Dentistry Clinic of North America. vol. 43, No. 4 (Oct. 1999), pp. 599-614, v-vi. PubMed Abstract only. [retreived on Jun. 8, 2007]. Retrieved from the internet.*
Sciubba, J.J. Oral Cancer: The Importance of Early Diagnosis and Treatment. American Journal of Clinical Dermatology, vol. 2, No. 4 (2001), pp. 239-251.*
Edgar et al. "Saliva Stimulation and Caries Prevention". Adv Dent Res, vol. 8, No. 2 (Jul. 1994) 239-245.*
"Halitosis—Treating Bad Breath" Internet Archive date: May 26, 1998 [retrieved on Nov. 20, 2007]. Retrieved from the Internet: <URL: http://web.archive.org/web/*/http://www.qualitydentistry.com/dental/halitosis/treatment.html>, p. 1.*
What are the basic ingreidents of toothpaste?: Ask Yahoo, Thursday, Sep. 28, 2000. Internet Archive date: Nov. 16, 2000. [retrieved on Aug. 8, 2007]. Retrieved from the Internet: <URL: http://web.archive.org/web/*/http://ask.yahoo.com/20000928.html, p. 2>.*
Edgar et al. "Saliva Stimulation and Caries Prevention". Adv Dent Res, vol. 8, No. 2 (Jul. 1994) 239-245).*
"Halitosis—Treating Bad Breath" <http://web.archive.org/web/*/http://www.qualitydentistry.com/dental/halitosis/treatment.html>.*
Nakatsu et al. "Biological Activity of Essential Oils and their Constituents." in: Rahman, Atta-ur-, Studies in Natural Products Chemistry vol. 21: Bioactive Natural Products (Part B) (The Netherlands, Elsevier Science B.V., 2000), pp. 571. 584.*
Quesnel et al.. "Synergism between Chlorhexidine and Sulphadiazine", J. of Appl. Bact. vol. 45, pp. 397, 400-405 (1978).
Riedl, "Core Alkylation of Phloroacylophenones", (Ber. vol. 89; p. 1863 (1956).
Carson, J "The Hydrogenation of Lupulone and Humulone" Am. Chem. Soc. vol. 73, p. 1850 (1951).

* cited by examiner

*Primary Examiner* — Amy L Clark
(74) *Attorney, Agent, or Firm* — Howard C. Lee

(57) ABSTRACT

An efficacious antibacterial and anti-inflammatory oral composition is provided having an active ingredient combination comprising one or more active compounds from an extract of *magnolia* and an extract of hops. Preferably, the active compounds from *magnolia* extract comprise honokiol and magnolol, and the active compounds from hops extract comprise hexahydrogenated beta acids. The oral composition can be in the form of a mouth rinse or dentifrice, including toothpaste, gels, powders, confectionaries, lozenges, animal products, and the like. Methods of making and using the oral composition are also provided.

5 Claims, No Drawings

ORAL CARE COMPOSITIONS CONTAINING COMPOUNDS FROM MAGNOLIA AND HOPS EXTRACTS

CROSS REFERENCE TO RELATED APPLICATION

This application claims priority to U.S. Provisional Patent Application No. 60/639,330, filed Dec. 22, 2004, the contents of which are incorporated herein by reference.

BACKGROUND OF THE INVENTION

Dental plaque is a soft deposit which forms on the surfaces of teeth. Plaque is comprised of an accumulation of bacteria and bacterial by-products. Dental plaque is generally believed to be formed as a byproduct of bacterial growth and comprises a dense microbial layer consisting of a mass of microorganisms embedded in a polysaccharide matrix. Plaque tenaciously adheres to the surfaces of teeth, especially along irregular and rough surfaces, and is typically found at the gingival margin, in cracks in the enamel, and on the surface of built-up dental calculus.

Gingivitis is the inflammation or infection of the gums and the alveolar bones that support the teeth. Gingivitis is generally believed to be caused by bacteria in the mouth (particularly the bacteria instigated in plaque formation) and the toxins formed as by products from the bacteria. Periodontitis is generally believed to occur where unremoved plaque hardens into calculus (tartar) which effects the periodontal ligaments. Periodontitis is a progressively worsened state of disease as compared to gingivitis. As plaque and calculus continue to build up, the gums begin to recede from the teeth and pockets form there between, which ultimately may result in destruction of the bone and periodontal ligament. These reactions lead to the destruction of the supporting structure, continued infection, and potentially the subsequent loss of teeth.

A wide variety of antibacterial agents have been suggested in the art to retard plaque formation and the oral infections associated with plaque formation. It is difficult to predict the antiplaque efficacy of antibacterial compounds when incorporated into an oral care composition with other active ingredients. Further, many antibacterial agents negatively interact with one or more components in the oral care delivery vehicle. Notwithstanding the efficacy of certain antibacterial agents, there is a continuing interest in the oral care field for oral care compositions which improve the treatment of both plaque and tartar formation, as well as to reduce the inflammation associated with gingivitis and periodontitis. It would be advantageous to have an active agent that is efficacious to combat plaque and diseases of the oral cavity, and further has anti-inflammatory effects in the oral cavity. Additionally, oral compositions that contain natural or botanically-based active ingredients are desirable.

BRIEF SUMMARY OF THE INVENTION

The invention provides an oral care composition that containing and ingredients that comprises a compound from an extract of *magnolia* and a compound from an extract of hops. Also provided is a method of preventing the formation of plaque on an oral surface in a mammalian subject comprising: (a) contacting the oral care to an oral surface; and (b) repeating (a) over a period of plurality of days.

In another embodiment, the invention provides a method of maintaining oral health in a mammalian subject, the method comprising: (a) preparing an oral care composition comprising an active ingredient that comprises a compound from an extract of *magnolia* and a compound from an extract of hops, and (b) contacting said oral care composition to an oral surface.

DETAILED DESCRIPTION OF THE INVENTION

In accordance with the present invention, an antiplaque, antigingivitis, and anti-inflammatory oral composition is provided that has a combination of one or more active compounds isolated from an extract of *magnolia* with one or more active compounds isolated from an extract of hops. The oral compositions of the present invention inhibit the growth of various oral bacteria that are implicated in forming plaque and causing oral diseases. For example, the oral compositions of the present invention are bactericidal against representative oral bacteria, such as *S. mutans, F. nucleatum, V. parvula, A. naeslundii*, and *P. gingivitis* as measured by the in vitro test Minimal Inhibitory Concentration (MIC). The oral composition of the present invention is applied to the oral surfaces in the oral cavity, and promotes overall oral health, including preventing plaque formation, caries formation, calculus formation, halitosis, gingivitis, and periodontitis, for example. For example, in an embodiment of the present invention, where an oral care composition comprises an orally acceptable delivery carrier and a safe and effective amount of the combination of an extract of hops and an extract of *magnolia*, it has been observed that the antibacterial activity is highly efficacious against both gram-positive and gram-negative bacteria.

Components of the oral composition include extracts of the *Humulus lupulus* plant. Such extracts include hops acids, such as alpha acid, beta acids, isoalpha acids, rho-isoalpha acids, tetrahydro-isoalpha acids, and hexahydro-isoalpha acids.

The compositions of the present invention comprise at least one active compound found in an extract of hops. As referred to here, such an "extract" of hops is an extract from dried hops flower, tendril, vine, or other part of a plant from the Cannabaceae family, in particular from the *Humulus lupulus* plant, (hereinafter "hops"), or a synthetic or semi-synthetic equivalent of such an extract or an active component thereof. In certain embodiments of the present invention, the active ingredient in the oral composition comprises one or more active compounds that have been isolated from an extract of hops. In other embodiments, the antibacterial ingredient comprises an extract of hops that contains one or more active compounds. The terms hops extract (which includes the extract and at least one active compound) and one or more active compounds from an extract of hops are used interchangeably herein.

Thus, in accordance with the present invention, hop acids are extracted from the hop plant by any of a variety of suitable extraction methods known to one of skill in the art. One major active compound within the hops extract is the organic acid humulone, also generally referred to as alpha acid. Alpha acids constitute about 10 to 15 percent by weight in dry hops and over 50 percent by weight of carbon dioxide hops extract.

Exemplary hops acids that may be used in the composition of the invention include humulone, lupulone, and colupulone, the structures of which are shown below.

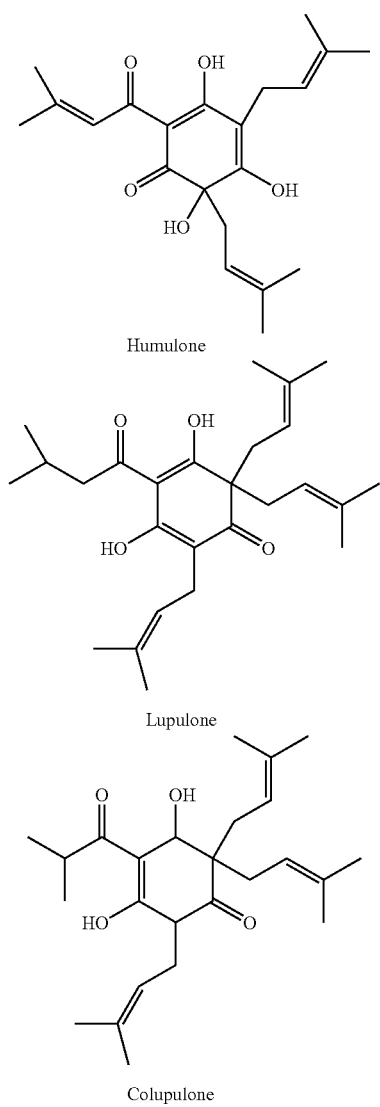

Humulone

Lupulone

Colupulone

In various embodiments, the selected hops extract(s) preferably comprises hydrogenated beta acids, including lupulones and colupulones, derivatives and analogs thereof as well as pharmaceutically acceptable salts thereof.

Also included are hexahydrobeta acids ("HHBA") such as hexahydrolupulone and hexahydrocolupulone and mixtures thereof. In certain embodiments, the preferred active compounds from hops extract may be the hydrogenated HHBAs.

Hydrogenated lupulones may be prepared by any means known in the art including the methods described by Riedl (Ber. 89:1863 (1956) or by Carson (J. Am. Chem. Soc. 73:1850 (1951)) or described in U.S. Pat. No. 5,082,975, the contents of each of which are incorporated herein by reference.

Additionally, the concentration of hops extract in the oral care composition depends upon the relative concentration of the active compounds in the extract, and as such, it is contemplated that the amount of hops extract or active compounds present may vary as recognized by one of skill in the art. For example, a mixture of hydrogenated beta acids (HHBA) useful in the present invention comprises lupulones (namely hexahydrolupulone at 35% by weight and hexahydrocolupulone at 65% by weight). Such mixtures may be obtained commercially, such as from Haas Hop Products, Inc., of Washington, D.C., U.S.A.

As it is understood in the art, the amount to be included in the composition should be safe and effective e.g., microbial growth, at the target site of a host to be treated, without undue adverse side effects (such as toxicity, irritation, or allergic response), commensurate with a reasonable benefit/risk ratio when used in the manner of this invention. The specific "safe and effective amount" will vary with such factors as the particular condition being treated, the physical condition of the patient, the duration of treatment, the nature of concurrent therapy (if any), the specific dosage form to be used, the excipient employed, the solubility of the active ingredient therein, and the dosage regimen desired for the oral composition.

In various embodiments, the hops extract or one or more of its active compounds are used to prepare oral compositions of the present invention, such as, dentifrices, gels and mouthrinses. The concentration of antibacterial ingredient containing at least one active compound derived from a hops extract in the oral care composition depends upon the relative concentration of the active compounds in the extract, or purity of the compounds, and as such, it is contemplated that the amount of hops extract or active compounds present may vary as recognized by one of skill in the art. Additionally, the concentration of the active ingredients is typically dependent upon the form of the oral composition. For example, mouthrinses typically have a relatively low concentration of an active ingredient, as where dentifrices, gels, or toothpowders have a higher concentration to achieve the same delivered dosage based on ease of dispersion. Likewise, confectionary compositions typically have a relatively high concentration of active ingredient to enable sufficient dispersion as they dissolve or are masticated.

In certain embodiments, the one or more active compounds (which may be included in the form of a hops extract or hops extract derivative) are incorporated in the oral composition in a safe and effective amount, typically in a range of about 0.001 to about 10 weight % of the total oral composition. In other embodiments, the one or more active compounds or the entire extract of hops is at a concentration of from between about 0.001 to about 3%. In another embodiment, the one or more active ingredients comprise less than 1% of the oral composition, and in certain embodiments are between about 0.02 to about 1% by weight.

The compositions of the present invention contain at least one active compound found in an extract of *magnolia*. As referred to here, such an "extract" of *magnolia* is an extract from dried cortex, or bark, of a plant from the Magnoliaceae family, such as *Magnolia officinalis*, (hereinafter "*magnolia*") or a synthetic or semi-synthetic equivalent of such an extract or an active component thereof. In certain embodiments of the present invention, the antibacterial ingredient in the active composition comprises one or more active compounds that have been isolated from an extract of *magnolia*. In other embodiments, the antibacterial ingredient comprises an extract of *magnolia*. The terms *magnolia* extract (which includes the extract and at least one active compound) and one or more active compounds from an extract of *magnolia* are used interchangeably herein.

Preferably, extracts of *Magnolia* Cortex (the bark of *Magnolia officinalis*) contain active compounds including: magnolol, honokiol, tetrahydromagnolol, and tetrahydrohonokiol, which have demonstrated bactericidal properties against representative oral bacteria *S. mutans, F. nucleatum, V. parvula, A. naeslundii, P. gingivitis* in the in vitro test Minimal Inhibitory Concentration (MIC). It should be noted that any plant from the Magnoliaceae family is suitable for the present invention and may be used in alternate embodiments. Preferably such that the extract comprises an antimicrobially effective concentration of a compound selected from the group consisting of magnolol, honokiol, tetrahydromagnolol, tetrahydrohonokiol, and mixtures thereof.

In one embodiment, the extract of *magnolia* may be obtained from dried *Magnolia* plant bark and can be prepared by any means known or to be developed in the art.

In various embodiments, it is preferred that the *magnolia* extract contains magnolol, honokiol, or both, the structure of each which are sown below.

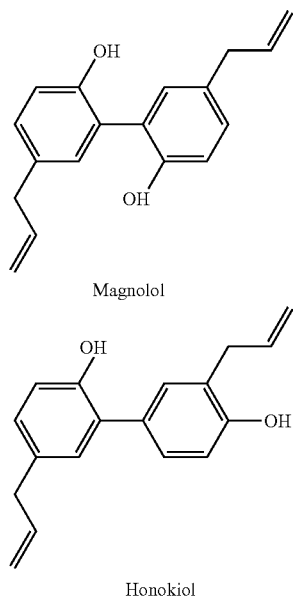

Magnolol

Honokiol

Additionally, tetrahydromagnolol and tetrahydrohonokiol hydrogenated analogs of magnolol and honokiol may be preferred or included in the composition as part of the extract.

In various embodiments, the *magnolia* extract of the present invention may be comprised of magnolol from about 2% to about 95%. In one embodiment, the magnolol may be present in the extract from about 5 to about 50%. In certain embodiments, magnolol may be present in the extract from about 30-50%. In various embodiments of the present invention, the honokiol may be present in the extract from about 2 to about 95%. In one embodiment of the present invention, the honokiol may be present in the extract from about 5 to about 50%. In certain embodiments honokiol may be present in the extract from about 30-50%.

In various embodiments of the present invention, the oral care composition comprises a safe and effective amount of one or more active compounds from the *magnolia* extract. Additionally, the concentration of one or more active compounds (or the *magnolia* extract containing the active compounds) in the oral care composition depends upon the relative concentration of the active compounds in the extract, and as such, it is contemplated that the amount of *magnolia* extract present may vary as recognized by one of skill in the art. In various embodiments of the present invention, one or more active compounds (or the *magnolia* extract itself) are present in the oral care composition from about 0.001 to about 10%. In one embodiment, one or more active compounds or the *magnolia* extract are present in the oral care composition from about 0.01 to about 3%. In other embodiments, the active compound(s) or *magnolia* extract are present at less than 1%, for example the extract is present at a concentration of from about 0.01 to about 1%. In one preferred embodiment, the one or more active compounds or *magnolia* extract are present in the oral care composition at a concentration of about 0.3%.

In various embodiments, the composition is an oral care composition that contains an active ingredient comprising one or more active compounds from a *magnolia* extract and one or more active compounds from a hops extract. However, additional antibacterial, anti-oxidant and/or antinflammatory active ingredients may be included in the oral care compositions. If added, the antibacterial active ingredients should not react with or detract from the efficacy and bioavailability of the *magnolia* extract.

Suitable antibacterial, anti-inflammatory, and/or anti-oxidant agents for use in addition to the *magnolia* and hops extracts of the present invention include any known in the art, botanical or synthetic, vitamins, proteinoid agents, peptides, minerals, salts and/or brologics.

Other natural extracts that are known antimicrobial agents are those listed in the International Cosmetic Ingredient Dictionary and Handbook, Tenth Ed., 2004, the contents of which are incorporated herein by reference.

In various embodiments, the additional agents added to the oral composition of the present invention comprise from about 0.0001% to about 10%, preferably from about 0.001% to about 5%, more preferably from about 0.01% to about 3%, depending on the concentration of the active compounds and form of the oral composition.

In certain embodiments, the oral compositions of the present invention optionally comprise one or more additional active ingredients. Such material may be operable for the prevention or treatment of a condition or disorder of hard or soft tissue of the oral cavity, the prevention or treatment of a physiological, localized or systemic disorder or condition, or to provide a cosmetic benefit. Optional oral care actives among those useful herein include antibacterial agents, anti-plaque agents, anti-adhesion, anti-oxidant, anticaries agents, anti-inflammatory agents, densensitizing agents, whitening agents, tartar control agents, periodontal actives, nutrients, abrasives, breath freshening agents, malodour control agents, tooth desensitizers, salivary stimulants, and combinations thereof, such as those known to one of skill in the art.

Various optional oral care actives may be included in the oral composition of the present invention including those described above, such as antibacterial agents, antiplaque agents, anti-adhesion (that prevent adhesion of plaque to an enamel surface), anti-oxidant (such as Vitamin E or coenzyme Q10), anticaries agents, densensitizing agents (such as potassium citrate, potassium tartrate, potassium chloride, potassium sulfate and potassium nitrate), whitening agents (such as, urea peroxide, sodium percarbonate, sodium perborate and polyvinylpyrrolidone-$H_2O_2$); compatible enzymes; anti-inflammatory agents (such as, steroidal agents including flucinolone and hydrocortisone, and nonsteroidal agents (NSAIDs)), tartar control agents, periodontal actives, chlorophyll compounds, nutrients (such as vitamins, minerals, and amino acids, lipotropics, fish oil, coenzymes and the like) abrasives, breath freshening/malodour control agents (such as zinc salts such as zinc gluconate, zinc citrate, zinc chlorite, and α-ionone), and salivary stimulants (such as such as citric, lactic, malic, succinic, ascorbic, adipic, fumaric and tartaric acids); and any other suitable ingredients for oral care known to one of skill in the art.

In various embodiments, the oral compositions of the present invention comprise antitartar agents to prevent and/or minimize calculus formation. One or more of such agents can be present.

Suitable anticalculus agents include without limitation: phosphates and polyphosphates. Phosphate and polyphosphate salts are generally employed in the form of their wholly or partially neutralized water soluble cationic species (e.g., potassium, sodium or ammonium salts, and any mixtures thereof). Thus, useful inorganic phosphate and polyphosphate salts illustratively include monovalent cations with monobasic, dibasic and tribasic phosphates; tripolyphosphate and tetrapolyphosphate; mono-, di-, tri- and tetra-pyrophosphates; and cyclophosphates (also generally known in the art as "metaphosphates"). Useful monovalent cations of such phosphate salts include hydrogen, monovalent metals including alkali metals, and ammonium, for example.

Synthetic anionic polycarboxylates may also be used in the dentifrice compositions of the present invention as an efficacy enhancing agent for certain active ingredients, including antibacterial, antitartar or other active agents within the oral composition. Such anionic polycarboxylates are generally employed in the form of their free acids or preferably partially or more preferably fully neutralized water soluble alkali metal (e.g. potassium and preferably sodium) or ammonium salts. As discussed above, preferred copolymers are of maleic anhydride or acid with another polymerizable ethylenically unsaturated monomer, preferably methylvinylether/maleic anhydride having an approximate molecular weight (M.W.) of about 30,000 to about 2,500,000 most preferably about 30,000 to about 2,000,000. Examples of these copolymers are available from ISP corporation under the tradename GANTREZ e.g. AN 139 (M.W. 1,100,000), AN 119 (M.W. 200,000); S-97 Pharmaceutical Grade (M.W. 1,500,000), AN 169 (M.W. 2,000,000), and AN 179 (M.W. 2,400,000); wherein the preferred copolymer is S-97 Pharmaceutical Grade (M.W. 1,500,000).

The anionic polycarboxylate, is employed in certain embodiments in amounts effective to achieve the desired enhancement of the efficacy of any antibacterial, antitartar or other active agent within the dentifrice composition. Generally, the anionic polycarboxylates is present within the dentifrice composition from about 0.05% to about 5% by weight, preferably from about 0.5% to about 2.5% by weight.

Orally acceptable carriers for use in the invention include the usual components of toothpastes, tooth powders, prophylaxis pastes, mouth rinses, lozenges, gums and the like, and are more fully described hereinafter. Selection of specific carrier components is dependant on the desired product form, including dentifrices, rinses, gels, and confectionaries.

As recognized by one of skill in the art, the oral compositions of the present invention optionally include other materials, such as for example, viscosity modifiers, diluents, surface active agents, such as surfactants, emulsifiers, and foam modulators, pH modifying agents, abrasives, humectants, emollients, and moisturizers, mouth feel agents, sweetening agents, flavor agents, colorants, preservatives and combinations thereof. It is understood that while general attributes of each of the above categories of materials may differ, there may be some common attributes and any given material may serve multiple purposes within two or more of such categories of materials. Preferably, such carrier materials are selected for compatibility with the active ingredient comprising an extract of *magnolia* and an extract of hops, as well as with other ingredients of the composition.

Thickeners

In various embodiments, such as for toothpastes, creams and gels, the oral composition contains a natural or synthetic thickener or gelling agent, which other than silica thickeners, include natural and synthetic gums and colloids. Such suitable thickeners include naturally occurring polymers such as carrageenans, xanthan gum, synthetic thickener such as polyglycols of varying molecular weights sold under the trade name Polyox and cellulose polymers such as hydroxyethyl cellulose and hydroxypropyl cellulose. Other inorganic thickeners include natural and synthetic clays such as hectorite clays, lithium magnesium silicate (laponite) and magnesium aluminum silicate (Veegum). Other suitable thickeners are synthetic hectorite, a synthetic colloidal magnesium alkali metal silicate complex clay available for example as Laponite (e.g., CP, SP 2002,D) marketed by Laporte Industries Limited. Laponite D analysis shows, approximately, 58.00% $SiO_2$, 25.40% MgO, 3.05% $Na_2O$, 0.98% $Li_2O$, and some water and trace metals, and has a true specific gravity of 2.53 and an apparent bulk density (g/mL at 8% moisture) of 1.0. In certain embodiments, the thickening agent is present in the dentifrice composition in amounts of about 0.1 to about 10%, preferably about 0.5 to about 5.0%. Other suitable thickeners include Irish moss, gum tragacanth, starch, polyvinylpyrrolidone, hydroxyethyl propyl cellulose, hydroxybutyl methyl cellulose, hydroxypropyl methyl cellulose, hydroxyethyl cellulose (e.g., available as Natrosol), sodium carboxymethyl cellulose, and colloidal silica such as finely ground Syloid (e.g., 244).

In various embodiments, the present invention provides a method of promoting oral health in an oral cavity and for treating plaque and gingivitis on an oral surface of a mammalian subject. The method comprises preparing an oral care composition comprising an orally acceptable vehicle and one or more active compounds from an extract of *magnolia* and one or more active compounds from an extract of hops. Then, the oral care composition is contacted with one or more oral surfaces of the oral cavity. In certain embodiments, when the oral composition is contacted with one or more oral surfaces in the oral cavity, the oral composition has the effect of reducing inflammation of oral tissue.

Thus, in various embodiments of the present invention, the oral care composition that is prepared is a dentifrice, confectionary, or mouthwash, The oral composition is preferably applied regularly to an oral surface, preferably on a daily basis, at least one time daily for multiple days, but alternately every second or third day. Most preferably the oral composition is applied to the oral surfaces from 1 to 3 times daily, at a pH of about 4.5 to about 10, generally about 5.5 to about 8, preferably about 6 to 8, for at least 2 weeks up to 8 weeks or more up to lifetime.

The oral compositions of the present invention may be prepared by suitably mixing the ingredients. For instance, in the preparation of a mouthrinse, antibacterial active ingredient comprising *magnolia* and hops extracts is dispersed in a flavor oil or an alcohol and then added to a mixture of humectants, surfactants, and water. The resulting rinse product is then packaged. Dentifrices are prepared by adding various salts (including fluoride), and sweeteners (e.g., saccharin) to water, where it is mixed. Into another container, all humectants, gums, and polymers are added together. The water mixture described above is added to the container with the humectants, gums, and polymers. The combined ingredients are optionally heated to about 140° to about 160° F. to disperse the gums and polymers. The heated mixture is then cooled to ambient temperatures. The mixture is then combined with abrasives, where it is mixed at high speed under a vacuum for 15 to 20 minutes. The flavor oil (and/or alcohol)

and active ingredient is then added to the mixture and mixed under high speed and vacuum until sufficiently dispersed. The surfactant(s) are added and the mixture is again mixed to disperse.

The oral composition of this invention can be incorporated into confectionary and tropes. Such methods of forming confectionary (e.g., gum) or tropes (e.g., lozenges) are well known by one of skill in the art, and can be prepared by stirring the extracts into a warm gum base or coating the outer surface of a gum base (for example, jelutone, rubber latex, vinylite resins, inter alia), desirably with conventional plasticizers or softeners, sugar or other sweeteners or carbohydrates such as glucose, sorbitol and the like. Other conventional additives including humectants, thickeners, surface active agents, water and flavorants may be included as desired.

The following Examples further illustrate the present invention, but it is understood that the invention is not limited thereto. All amounts and proportions referred to herein and in the appended claims are by weight unless otherwise indicated.

EXAMPLE I

A dentifrice formulation is prepared containing an antibacterial active ingredient combining 0.3% *magnolia* extract extracted with HFA-13A, and 0.3% of a hops extract extracted by supercritical $CO_2$ containing a mixture of HHBAs (hexahydrolupulone at 35% by weight, hexahydrocolupulone at 65% by weight, and having 96% purity) available from John I. Haas, Inc., of Washington, D.C. Further, additional active tartar control active ingredients were added containing tetrasodium pyrophosphate (TSPP), sodium tripolyphosphate (STPP). A copolymer of maleic anhydride and methyl vinyl ether (Gantrez S97 liquid) was also added with the ingredients listed in Table I.

A dentifrice composition having the ingredients listed in Table I is prepared by the following method. Sodium saccharin, sodium fluoride, tetrasodium pyrophosphate (TSPP), sodium tripolyphosphate (STPP), and any other salts are dispersed in water. The humectants e.g., glycerin and sorbitol, are added to the mixture in a conventional mixer under agitation. The resultant mixture is agitated until a homogeneous gel phase is formed. A pigment such as $TiO_2$ is added into the gel phase, and any acid or base (e.g., NaOH) required to adjust the pH to 6 to 7. Then organic thickeners, carrageenan, and CMC, are added. These ingredients are mixed until a homogenous phase is obtained. The mixture is then transferred to a high-speed vacuum mixer; where the silica abrasives, and the silica thickener are added. The mixture is then mixed at high speed for from 5 to 30 minutes, under vacuum of from about 20 to 50 mm of Hg, preferably about 30 mm Hg. The flavor oil is weighed out and the hops and *magnolia* extracts are then added to the flavor oil. The flavor oil and *magnolia*/hops mixture is added to the mixture. Surfactants, such as sodium lauryl sulfate (SLS) are added last. The resultant product is a homogeneous, semi-solid, extrudable paste or gel product.

TABLE I

| Ingredient | Final Wt. % |
| --- | --- |
| Hop Acids Extract (HHBA) | 0.3 |
| Magnolia Cortex Extract | 0.3 |
| TSPP | 1.0 |
| STPP | 7.0 |
| GANTREZ S97- liquid solution | 1.0 |
| Sorbitol | 18.69 |
| Glycerin | 12.0 |
| Sodium fluoride | 0.243 |
| Sodium saccharin | 0.3 |
| Sodium hydroxide | 1.0 |
| CMC 2000S | 0.8 |
| Carrageenan (LB 9505) | 0.4 |
| SYLODENT 783 | 11.0 |
| SYLODENT XWA 650 | 10.0 |
| Zeodent 165 | 3.5 |
| Sodium lauryl sulfate | 1.2 |
| $TiO_2$ coated Mica | 0.1 |
| Flavor (89-332) | 1.0 |
| Blue Color Solution | 0.05 |
| Water | Q.S. |

The description of the invention and examples provided herein is merely exemplary in nature and, thus, variations that do not depart from the gist of the invention are intended to be within the scope of the invention. Such variations are not to be regarded as a departure from the spirit and scope of the invention.

What is claimed is:

1. An oral care composition comprising:
   at least one active compound found in an extract of *magnolia*, wherein said at least one active compound is selected from the group consisting of: magnolol, honokiol, tetrahydromagnolol, tetrahydrohonokiol, and combinations thereof; and
   at least one active compound found in an extract of hops selected from the group consisting of hexahydrolupulone and hexahydrocolupulone,
   wherein the at least one active compound found in the extract of *magnolia* is present in the oral composition at a concentration of about 0.3% by weight, and
   the at least one active compound found in the extract of hops is a mixture of hexahydrolupulone and hexahydrocolupulone and is present in the oral composition at a concentration of about 0.3% by weight, and wherein said oral care composition is in the form of a gel.

2. The composition according to claim 1, wherein the at least one active compound found in the extract of *magnolia* comprises honokiol in an amount of about 2 weight % to about 95 weight %.

3. The composition according to claim 1, wherein the hexahydrolupulone is present in an amount of about 35 weight %.

4. The composition according to claim 1, wherein the hexahydrocolupulone is present in an amount of about 65 weight %.

5. The composition according to claim 1, further comprising an ingredient selected from: an anti-adhesion agent, an anti-oxidant, an anticaries agent, a desensitizing agent, a whitening agent, a tartar control agent, a periodontal active, an abrasive, a breath freshening agent, a malodour control agent, a salivary stimulant, a viscosity modifier, a diluent, a surface active agent, a pH modifying agent, a humectant, a mouth feel agent, a sweetening agent, a flavor agent, a colorant, a preservative, a vitamin, a compatible enzyme, a chlorophyll compound, and a combination of two or more thereof.

* * * * *